United States Patent [19]
Hajianpour

[11] Patent Number: 6,123,704
[45] Date of Patent: Sep. 26, 2000

[54] SUPPORT FIXTURE FOR SETTING A FRACTURED DISTAL RADIUS

[76] Inventor: Mohammed A. Hajianpour, 1706 Vestal Dr., Coral Springs, Fla. 33071

[21] Appl. No.: 09/338,034

[22] Filed: Jun. 22, 1999

[51] Int. Cl.⁷ .................................................. A61B 17/56
[52] U.S. Cl. .................................................. 606/54
[58] Field of Search ................................ 606/54, 57, 59, 606/69, 60, 71

[56] References Cited

U.S. PATENT DOCUMENTS

| | | | |
|---|---|---|---|
| 4,554,915 | 11/1985 | Brumfield | 128/92 A |
| 4,714,076 | 12/1987 | Comte et al. | 128/92 |
| 4,747,400 | 5/1988 | Koeneman et al. | 128/92 Z |
| 5,006,120 | 4/1991 | Carter | 606/69 |
| 5,074,291 | 12/1991 | Carter | 606/241 |
| 5,250,048 | 10/1993 | Gundolf | 606/69 |
| 5,545,162 | 8/1996 | Huebner | 606/57 |
| 5,683,389 | 11/1997 | Orsak | 606/59 |
| 5,741,251 | 4/1998 | Benoist | 606/54 |

OTHER PUBLICATIONS

Henry Gray, F.R.S., Anatomu, Descriptive and Surgical, Facsimile of the 1901 edition, reproduced by Barnes & Nobel Books, 1995, p. 389.

Henry Gray, F.R.S., Anatomy, Descriptive and Surgical, Facsimile of the 1901 edition, reproduced by Barnes & Noble Books, 1995, p. 389.

*Primary Examiner*—Michael Buiz
*Assistant Examiner*—Vy Q. Bui
*Attorney, Agent, or Firm*—Ronald V. Davidge

[57] ABSTRACT

A support fixture for setting a fractured distal radius includes a housing having a strap for fastening the fixture to the patient's forearm, a sliding section, sliding within the housing as a screw is rotated, and a pivoting section extending from a distal end of the sliding section. The sliding section also includes a structure for supporting the patient's wrist. The distal end of the pivoting section includes a pair of fingertraps. Two of the patient's fingers are held in the fingertraps, while an extension force is applied between his forearm and hand through the rotation of the screw, and while his hand is twisted by adjusting the angle of the pivoting section to increase the gap between fractured sections of bone, causing reduction of the fracture to occur.

11 Claims, 2 Drawing Sheets

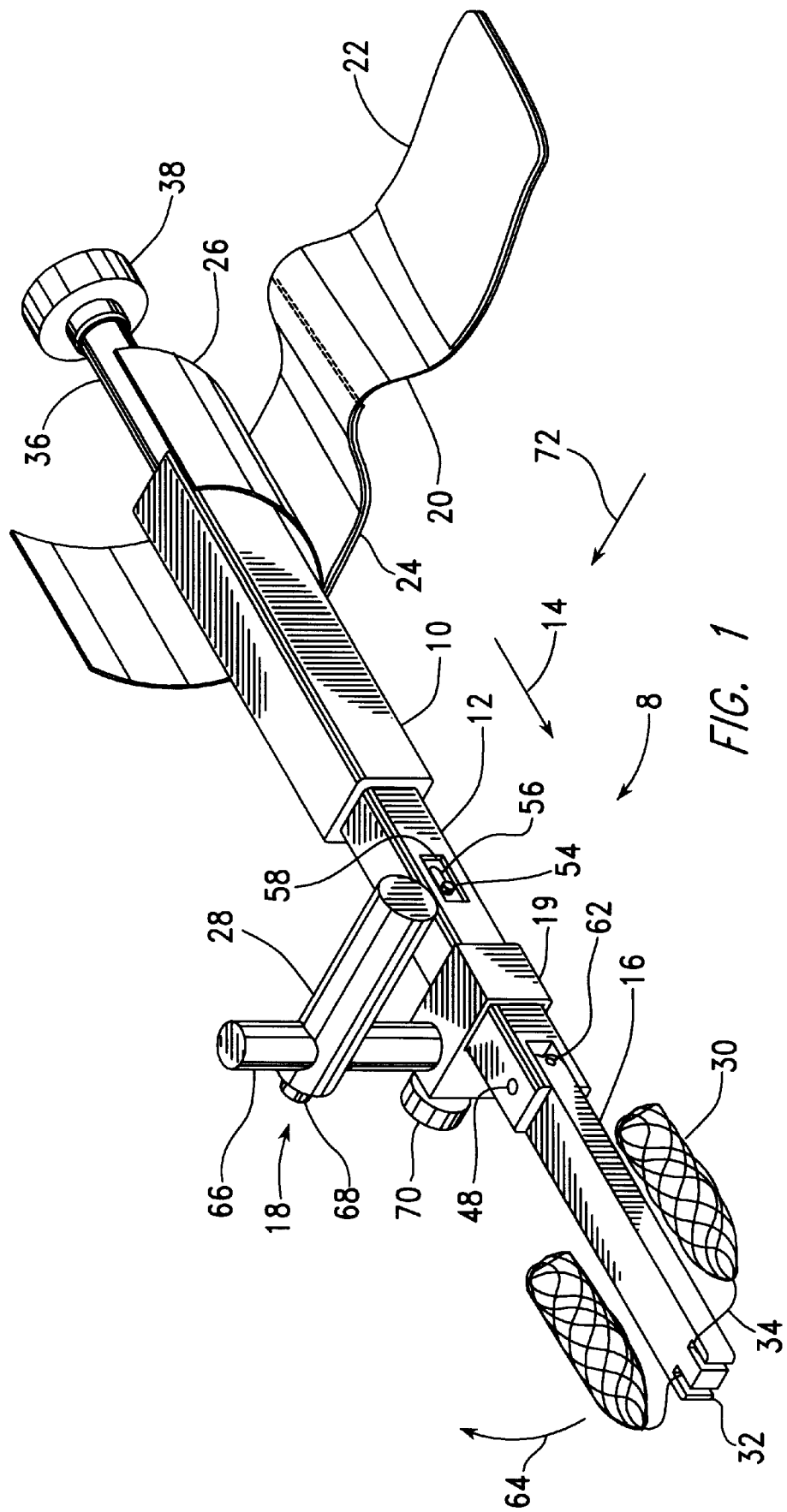

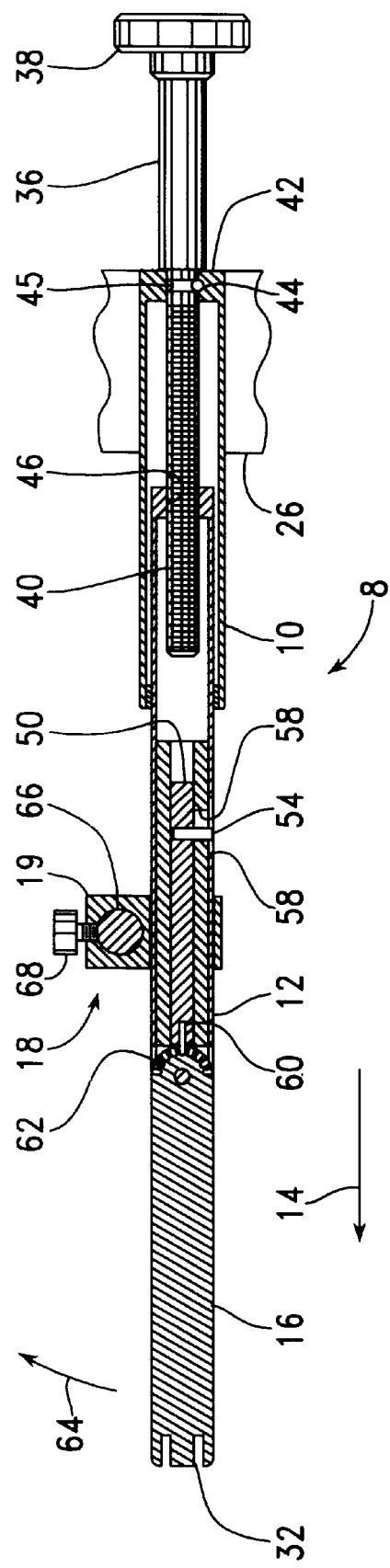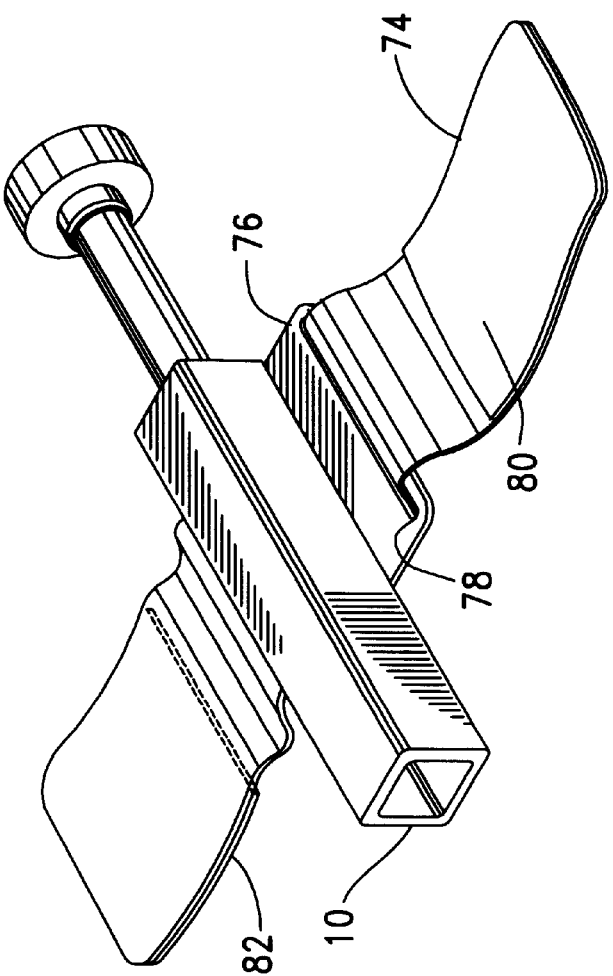

SUPPORT FIXTURE FOR SETTING A FRACTURED DISTAL RADIUS

BACKGROUND OF THE INVENTION

1. Field of the Invention

This invention relates to apparatus for use in the setting, or reduction, of a fractured distal radius.

2. Background Information

The fracture of the distal radius is one of the most common human fractures, occurring in as many as 350,000 people per year in the United States alone. The application of an extension force and lateral depression for reducing a fracture of the distal radius is well known, having been described in the 1901 edition of Gray's Anatomy in the following manner, "The treatment consists in flexing the forearm, and making a powerful extension from the wrist and elbow, depressing at the same time the radial side of the hand, and retaining the parts in that position by well-padded pistol-shaped splints."

Conventional methods for reducing a fractured distal radius require that the physician or surgeon must be helped by an assistant during the process. Two or more people are required to apply the extension force to the hand and elbow, to twist the hand into a configuration providing an additional extension force at the site of the fracture, and to further manipulate any bone fragments or separated sections into position. What is needed is a convenient fixture for applying such forces during the process of setting this type of fracture, so that a physician or surgeon can reduce the fracture without requiring the help of an assistant.

U.S. Pat. No. 5,006,120 shows the use of a device including a weight, a pulley, and fingertraps to hold a patient's arm extended, reducing a distal fracture of the radius during an operation installing, with a number of screws and blades extending into the bone, a plate spanning a fracture of the distal radius. What is needed, is a convenient means to support the wrist, from below and from a side, in a manner that the angle of the wrist can be controlled during the setting of such a fracture, and, for example, during the installation of a plate spanning a fracture of the distal radius.

U.S. Pat. Nos. 4,554,915 and 5,545,162 describe external fixation frames which are used, for example, for immobilizing bone segments adjacent a fracture or joint. Again, what is needed is a convenient means to support the wrist, from below and from a side, in a manner that the angle of the wrist can be controlled during the installation of an external fixation frame.

SUMMARY OF THE INVENTION

Thus, a first objective of the present invention is to provide a convenient means for applying a significant traction force between a patient's hand and forearm to facilitate the reduction of a distal radius fracture.

A second objective of the present invention is to provide a support for the wrist during the application of such a significant traction force.

A third objective of the present invention is to provide a means for varying the angle of the hand to aid in the generation of a traction force across a distal radius fracture.

A fourth objective of the present invention is to provide a support fixture, for reduction, which can easily be converted for application to either the right or left arm.

A support fixture for setting a fractured radius is configured for being tied to a patient's forearm and for applying adjustable traction to the wrist by means of the fingers. The support fixture also provides a vertically adjustable wrist support bar and means for varying the angular positioning of the hand.

According to a first aspect of the present invention, there is provided a support fixture for setting a fractured distal radius of a forearm. The support fixture includes a housing, a movable member, and a drive mechanism. The housing includes a drive support section and an attachment strap for attachment to a proximal portion of the forearm. The movable member, which is slidably mounted within the housing, includes a driven section and a first finger holder at a distal end of the movable member. The drive mechanism, which extends between the drive support section of the housing and the driven section of the movable member, moves the driven section of the movable member relative to the drive support section of the housing, causing the distal end of the movable member to be extended through a variable distance from the housing.

BRIEF DESCRIPTION OF THE FIGURES

FIG. 1 is an isometric view of a support fixture built in accordance with the present invention;

FIG. 2 is a longitudinal cross-sectional view of the support fixture of FIG. 1, taken as indicated by section lines II—II in FIG. 1; and FIG. 3 is an isometric view of a housing of the support fixture of FIG. 1, showing an alternative form of adjustable strap.

DETAILED DESCRIPTION OF THE INVENTION

FIG. 1 is an isometric view of a support fixture 8 for setting a fractured radius, built in accordance with the present invention. The support fixture 8 includes a housing 10, a sliding support member 12, which extends outward from the housing 10 in the distal direction of arrow 14, and a pivoting member 16, which is pivotally attached to extend from the sliding support member 12 at a variable angle, and a wrist support subassembly 18, which includes a block 19 slidably mounted on the sliding support member 12. The patient's forearm (not shown) is attached to the housing 10 by means of an adjustable strap 20, which is wrapped around the arm and attached to itself. To facilitate such attachment in an adjustable manner, a first attachment pad 22 is sewn to the inner surface of the end of the strap 20, while a second attachment pad 24 is fastened to the outer surface of the opposite end of the strap 20. One of these pads 22, 24 includes a number of VELCRO hooks, while the other of these pads 22, 24 includes a number of loops into which these hooks individually attach. The stable positioning of the patient's forearm to extend along the housing 10 is facilitated through the use of a "U"-shaped flexible clamping member 26, which is held inward, against the forearm, by means of the strap 20 to form a rigid clamping structure of suitable width. Both the clamping member 26 and the strap 22 are fastened to the lower surface of the housing 10 by means of attachment devices (not shown), such as screws.

The patient's wrist (not shown) extends over and along a wrist support bar 28, which forms part of the wrist support subassembly 18, while the patient's hand is held in place by means of a pair of finger traps 30 held within slots 32 the distal end of the pivoting member 16. Two fingers of the patient's hand are placed individually within the finger traps 30. Each of the finger traps 30 is a flexible wire device which tends to tighten on a finger over which it is placed as tension is placed on the trap 30 by means of the wire 34 with which it is attached to the pivoting member 16. The finger traps 30 may subsequently be removed when this tension is relieved.

The distance through which the sliding member 12 extends from the housing 10 is adjusted by means of an adjustment screw 36, which includes a handle 38 and a threaded section 40 having an acme thread. This adjustment screw 36 is rotatably mounted within a proximal end cap 42 of the housing 10 by means of a pin 44 engaging a groove 45 in the adjustment screw 36. The threaded section 40 extends within an internally threaded hole 46 of a proximal end cap 48 of the sliding member 12. Thus, rotating the adjustment screw 36 in one direction causes the sliding member 12 to move in the distal direction of arrow 14, increasing the traction force applied to the patient's arm, while rotating the adjustment screw 36 in the opposite direction causes the sliding member 12 to move in the direction opposite to arrow 14, reducing or removing this traction force.

The pivoting member 16 is pivotally mounted to the sliding member 12 by means of a pin 48. The sliding member 12 also includes a locking member 50, which slides in a bushing 52 within the member 12. A button 54 extends from the sliding member 12 through an aperture 56 in the bushing 52 and through an aperture 58 in the sliding member 12, providing the user with an ability to move the locking member 50. When the sliding member 12 is moved in the distal direction of arrow 14, a pin 60 extending from the distal end of the locking member 50 enters a hole 62 within the pivoting member 16, provided the hole 62 is in alignment with the pin 60. A compression spring (not shown) may also be used to hold the locking member 50 with the pin 60 engaging a hole 62. The holes 62 are located so that the pivoting member 16 can be held in alignment with the sliding member 12 (in which it is shown), or in up to 80 degrees rotation in either direction from this position of alignment, with locking positions at every 20 degrees of rotation.

In the example of the figures, the support fixture 8 is assembled in a configuration for treatment of a distal fractured radius of the right arm. The patient's wrist is placed over wrist support bar 28, with the pivot arm 16 rotated and held in the direction of arrow 64, so that the edge of the wrist is held against vertical post 66 of wrist support subassembly 18. This action twists the wrist so that additional traction force is applied across the fracture to aid in its reduction. The wrist support bar 28 is vertically adjustable within the wrist support subassembly 18 when a clamping screw 68 is loosened, and the wrist support subassembly 18 is adjustable along the sliding member 12, in and opposite to the distal direction of arrow 14 when a clamping screw 70 is loosened. The adjustment screw 36 is rotated by means of knob 38 to apply a traction force to the hand, through the fingertraps 30, which is sufficient to reduce the fracture, pulling the bone segments on each side of the fracture into alignment.

Since the vertical post 66 extends along the side of the wrist opposite the radius, the side of the fractured radius is exposed, allowing the manual manipulation of bone fragments into alignment with the major bone segments which are being brought into alignment by traction force developed within the support fixture 8.

To convert the support fixture 8 for treatment of a distal fractured radius of the left arm, the wrist support subassembly 18 is removed over the distal end of pivoting member 16, rotated so that the wrist support bar 28 extends in the direction of arrow 72, and reinstalled over the distal end of pivoting member 16. For treating the left arm, the pivot arm 16 is rotated and held in the direction opposite to arrow 64. With these capabilities, the same apparatus can readily be used to treat similar fractures of either wrist.

The support fixture 8 is preferably composed of materials which are radiotransparent, so that, while the arm is held in the support fixture 8, X-ray films can be taken to show the orientation of bone sections and fragments, even when such bone structures are aligned with a portion of the support fixture 8.

FIG. 3 is an isometric view of the housing 10 having an alternative adjustable strap 74, which is wrapped around the patient's forearm (not shown) and attached to itself. The strap 74 is attached to the housing 10 by means of a plate 76 extending from each side of the housing 10 to provide a pair of slots 78 through which the strap 74 extends. Again, to facilitate the attachment of the strap 74 to the patient's forearm in an adjustable manner, a first attachment pad 80 is sewn to the inner surface of the end of the strap 74, while a second attachment pad 82 is fastened to the outer surface of the opposite end of the strap 74. One of these pads 80, 82 includes a number of VELCRO hooks, while the other of these pads 80, 82 includes a number of loops into which these hooks individually attach.

The support fixture 8 may be used in the reduction of a distal radius fracture which is immobilized within a cast, which is immobilized by means of an external fixation frame, such as that described in U.S. Pat. No. 4,554,915, or which is repaired using screws and a plate, such as that described in U.S. Pat. No. 5,006,120. The support fixture 8 is configured to expose the hand and wrist in the area of the fractured radius in such a manner that an external fixation frame may be installed with the arm remaining in the support fixture 8 and in such a manner that a plate may be installed during an operation with the arm remaining in the support fixture 8. The features of the support fixture 8, such as varying the extension force applied by turning the knob 38, and varying the angle of the pivoting member 16 after releasing it using the sliding pin 54, may be used to position the hand and wrist as required for the installation of an external fixation frame or as required for an operation to install a plate.

While the invention has been described in its preferred form or embodiment with some degree of particularity, it is understood that this description has been given only by way of example and that numerous changes in the details of construction, fabrication and use, including the combination and arrangement of parts, may be made without departing from the spirit and scope of the invention.

I claim:

1. A support fixture for setting a fractured distal radius of a forearm, wherein said support fixture comprises:

a housing, including a drive support section and an attachment strap for attachment to a proximal portion of said forearm;

a movable member, slidably mounted within said housing, including a driven section and a first finger holder at a distal end of said movable member; and drive means, extending between said drive support section of said housing and said driven section of said movable member, moving said driven section of said movable member relative to said drive support section of said housing causing said distal end of said movable member to be extended through a variable distance from said housing.

2. The support fixture of claim 1, additionally comprising a wrist support structure mounted on said movable member.

3. The support fixture of claim 2, wherein said wrist support structure includes:
   wrist support post, attachable to extend upward from either side of said movable member;
   a wrist support bar, extending across said movable member, being slidably mounted on said wrist support post; and
   a clamp holding said wrist support bar in place on said wrist support post.

4. The support fixture of claim 1, wherein
   said movable member includes a sliding member, slidably mounted within said housing, and a pivoting member, pivotally mounted at a distal end of said sliding member, and clamped in place at an angle relative to said sliding member,
   said sliding member includes said driven section,
   said pivoting member includes said finger holder.

5. The support fixture of claim 4, additionally comprising a wrist support structure mounted on said movable member.

6. The support fixture of claim 5, wherein said wrist support structure includes:
   wrist support post, attachable to extend upward from either side of said sliding member;
   a wrist support bar, extending across said movable member, being slidably mounted on said wrist support post; and
   a clamp holding said wrist support bar in place on said wrist support post.

7. The support fixture of claim 1, wherein said first finger holder includes a first flexible wire fingertrap.

8. The support fixture of claim 7, wherein said movable member additionally includes a second finger holder having a second flexible wire fingertrap.

9. The support fixture of claim 1, wherein
   said drive means includes a drive screw including an externally threaded portion,
   said drive support section of said housing includes a bearing hole within which said drive screw rotates, and
   said driven section of said movable member includes an internally thread portion engaging said externally threaded portion of said drive screw.

10. The support fixture of claim 1, wherein said attachment strap includes a attachment pad having a pattern of hooks at a first end of said strap and on first side of said strap and a second attachment pad having a pattern of loops opposite said first end of said strap and opposite said first side of said strap.

11. The support fixture of claim 10, additionally including a flexible clamping member extending inside said strap.

* * * * *